United States Patent [19]

Miller et al.

[11] Patent Number: 5,192,783
[45] Date of Patent: Mar. 9, 1993

[54] 1-ARALKYL-1,2,4-TRIAZOLES

[75] Inventor: George A. Miller, Maple Glen, Hak-Foon Chan, Doylestown, both of Pa.

[73] Assignee: Rohm and Haas Company, Philadelphia, Pa.

[21] Appl. No.: 781,848

[22] Filed: Sep. 30, 1985

Related U.S. Application Data

[63] Continuation of Ser. No. 252,633, Apr. 9, 1981, abandoned, which is a continuation of Ser. No. 798,716, May 19, 1977, abandoned.

[51] Int. Cl.$^5$ ............... A01N 43/653; C07D 249/08; C07D 249/14
[52] U.S. Cl. ............................ 514/383; 514/184; 548/101; 548/262.2; 548/264.8; 548/265.2; 548/266.8; 548/267.2; 548/267.4; 548/267.8; 548/268.6
[58] Field of Search ............... 548/101, 262; 424/245, 424/269

[56] References Cited

U.S. PATENT DOCUMENTS

| | | | |
|---|---|---|---|
| 3,647,810 | 3/1972 | Bayer et al. | 548/262 |
| 3,647,914 | 3/1972 | Greenfield | 548/262 |
| 3,821,394 | 6/1974 | Timmler et al. | 548/341 |
| 3,897,438 | 7/1975 | Draber et al. | 548/262 |
| 3,927,017 | 12/1975 | Heeres et al. | 548/341 |
| 4,005,083 | 1/1977 | Buchel et al. | 548/262 |
| 4,598,085 | 7/1986 | Heeres, II et al. | 548/262 |

OTHER PUBLICATIONS

Ainsworth et al., J. Med. Pharm. Chem., vol. 5, pp. 383–389 (1962) RS1J5.

*Primary Examiner*—Patricia L. Morris
*Attorney, Agent, or Firm*—Terence P. Strobaugh

[57] ABSTRACT

This invention relates to 1 and 4-aralkyl-1,2,4-triazoles, their enantiomorphs, acid addition salts and metal salt complexes. This invention also relates to the method of preparation and use of these compounds. These compounds are highly active broad-spectrum systemic fungicides effective in controlling phytopathogenic fungi such as barley net blotch (*Helminthosporium teres*), grey mold (*Botrytis cinerea*), bean powdery mildew (*Erysiphe polygoni*), grape downy mildew (*Plasmopora viticola*), rice blast (*Piricularia oryzae*), tomato late blight (*Phytophthora infestans*) and wheat stem rust (*Puccinia graminis* f. sp. *tritici* race 15B-2).

29 Claims, No Drawings

1-ARALKYL-1,2,4-TRIAZOLES

CROSS REFERENCE TO RELATED APPLICATIONS

This is a continuation of U.S. application Ser. No. 252,633 filed Apr. 9, 1981, now abandoned, which is a continuation of U.S. application Ser. No. 798,716 filed May 19, 1977, now abandoned.

SUMMARY OF THE INVENTION

This invention relates to compounds of the formula

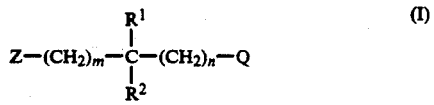

(I)

wherein Z is an aryl group; $R^1$ and $R^2$ are independently a hydrogen atom, an alkyl group, a cycloalkyl group, an alkenyl group, a cycloalkenyl group, an alkynyl group, an aryl group or an aralkyl group; or $R^1$ and $R^2$ are taken together with the carbon atom to which they are attached to form a cycloalkyl group; Q is a 1-(1,2,4-triazole) or a 4-(1,2,4-triazole) group; m is zero or the integer 1; n is the integer 1 or 2; and the agronomically acceptable enantiomorphs, acid addition salts and metal salt complexes thereof. This invention also relates to methods of preparation of the compounds and salts of this invention as well as their use as broad-spectrum fungicides.

DETAILED DESCRIPTION OF THE INVENTION

This invention relates to novel 1 & 4-aralkyl-1,2,4-triazoles and the enantiomorphs, acid addition salts and metal salt complexes thereof, as well as their method of preparation and their use as highly active broad-spectrum systemic fungicides. In particular, this invention relates to compounds of the formula

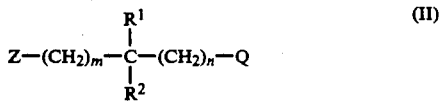

(II)

wherein Z is an optionally substituted ($C_6$ to $C_{10}$) aryl group; $R^1$ and $R^2$ are independently a hydrogen atom, a ($C_1$ to $C_{12}$) alkyl group, a ($C_3$ to $C_8$) cycloalkyl group, a ($C_2$ to $C_8$) alkenyl group, a ($C_5$ to $C_8$) cycloalkyl group, a ($C_2$ to $C_8$) alkynyl group, an optionally substituted ($C_6$ to $C_{10}$) aryl group, a ($C_7$ to $C_{14}$) aralkyl group the aryl portion of which is optionally substituted or $R^1$ and $R^2$ are taken together with the carbon atom to which they are attached to form a ($C_3$ to $C_8$) cycloalkyl group; Q is an optionally substituted 1-(1,2,4-triazole) or 4-(1,2,4-triazole); m is zero or the integer 1; n is the integer 1 or 2; and the agronomically acceptable enantiomorphs and acid addition salts thereof.

By the term "aryl", as used in defining the substituents Z, $R^1$ and $R^2$ in the present specification and claims, is meant preferably a phenyl or naphthyl group which is optionally substituted with up to three substituents, preferably up to two substituents selected from the group consisting of halogen, nitro, trihalomethyl, cyano, ($C_7$ to $C_{14}$) aralkyl, ($C_1$ to $C_4$) alkyl, ($C_1$ to $C_4$) alkoxy, ($C_1$ to $C_4$) alkylthio, ($C_1$ to $C_4$) alkylsulfinyl, ($C_1$ to $C_4$) alkylsulfonyl, phenoxy, phenylthio, phenylsulfinyl, phenylsulfonyl, and phenoxy, phenylthio, phenylsulfinyl or phenylsulfonyl substituted with up to two substituents selected from the group consisting of halogen nitro, trifluoromethyl, cyano, methyl, methoxy, methylthio, methylsulfinyl and methylsulfonyl.

Typical aryl substituents encompassed in this invention are phenyl, naphthyl, 4-chlorophenyl, 2,4-dibromophenyl, 3,5-difluorophenyl, 2,4,6-trichlorophenyl, 2,3,5-tribromophenyl, 3,4-dichlorophenyl, 2-chloro-4-iodophenyl, 3-chloro-4-nitrophenyl, 2,4-dinitrophenyl, 4-phenoxyphenyl, 2-phenylthiophenyl, 3-phenylsulfinylphenyl, 4-phenylsulfonylphenyl, 4-chlorophenoxyphenyl, 2,4-dibromophenoxyphenyl, 3,5-difluorophenylthiophenyl 4-chloro-2-methylphenylsulfinylphenyl, 3,4-diiodophenylthiophenyl, 4-trifluoromethyl-2-chlorophenyl-sulfonylphenyl, 2-cyano-4-methoxyphenylsulfinylphenyl, 4-methylthiophenoxyphenyl, 2-methylsulfinylphenylsulfinylphenyl, 4-methylsulfonyl-3-chlorophenoxyphenyl, 3,5,6-trimethylphenyl, 2-nitro-4-methoxyphenyl, 2-chloronaphthyl, 2-nitronaphthyl, 2,4-dimethoxyphenyl, 4-trifluoromethylphenyl, 2-nitro-4-trifluoromethylphenyl, 3,5-dimethylthiophenyl, 2-cyano-5-methylphenyl, 2,4-dimethylsulfinylphenyl, 2,4-dimethylsulfonylphenyl, 2,4-diiodonaphthyl, 2-iodo-4-benzylphenyl and the like.

The term "aralkyl" is used in defining the substituents $R^1$ and $R^2$ in the present specification and claims, to mean an aralkyl group wherein the alkyl chain is from 1 to 4 carbon atoms and the aryl group is meant to be defined as above. Typical aralkyl substituents encompassed in this invention are 2,4-dichlorobenzyl, 2,4-dibromobenzyl, 2,5-dinitrobenzyl, 2,4,6-trichlorobenzyl, 3,5-dimethoxyphenethyl, 2,5-dimethylthiophenylpropyl, 2,4-diiodophenyl-2-methyl-propyl, 3,4-dimethylsulfinylbenzyl, 2,3-dimethylsulfonylphenylethyl, 2,4,5-trimethylphenylbutyl, 2,4-dicyanonaphthylmethyl, 1-nitronaphthylethyl, 2-nitronaphthylpropyl, 2,4-dibromonaphthylbutyl and the like.

The term "alkyl", as utilized in defining $R^1$ and $R^2$ in the present specification and claims, is meant to include both branched and straight chained alkyl groups of from 1 to 12 carbon atoms. Typical alkyl groups which are encompassed by the use of this term in defining this invention are methyl, ethyl, propyl, iso-propyl, n-butyl, sec-butyl, iso-butyl, tert-butyl, pentyl, neopentyl, iso-pentyl, hexyl, heptyl, iso-octyl, nonyl, decyl, iso-decyl, undecyl, dodecyl and the like.

In the definition of Q, as used in the specification and claims, the term "optionally substituted 1-(1,2,4-triazole) or 4-(1,2,4-triazole)" is meant to include unsubstituted 1 & 4-(1,2,4-triazoles) and 1 & 4-(1,2,4-triazoles) which can be substituted with up to two substituents selected from the group consisting of halogen, ($C_1$ to $C_4$) alkyl, nitro and cyano.

The acids which can be utilized in making the acid addition salts of the present invention include hydrochloric, hydrobromic, nitric, sulfuric, phosphoric, hydroiodic, hydrofluoric, perchloric, p-toluenesulfonic, methanesulfonic, acetic, citric, tartaric, malic, maleic, oxalic, fumaric, phthalic and the like.

Another embodiment of this invention is the metal salt complexes of the formula

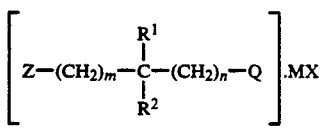

(III)

wherein Z, $R^1$, $R^2$, Q, m and n are as defined in Formula (II) above and M is a cation selected from Group IIA, IB, IIB, VIB, VIIB, and VIII of the periodic Table and X is an anion counterion selected in such a manner that the sum of the valence charges of the cation M and anion X equal zero.

Typical cations encompassed by this invention are magnesium, manganese, copper, nickel, zinc, iron, cobalt, calcium, tin, cadmium, mercury, chromium, lead, barium and the like.

Typical anions encompassed by this invention are chloride, bromide, iodide, fluoride, sulfate, bisulfate, perchlorate, nitrate, nitrite, phosphate, carbonate, bicarbonate, acetate, citrate, oxalate, tartarate, malate, maleate, fumarate, p-toluenesulfonate, methanesulfonate, (mono) or (di) ($C_1$-$C_4$) alkyl-dithiocarbamate, ($C_1$-$C_4$) alkylene-bis-dithio carbamate and the like.

A preferred embodiment of this invention is the compounds, salts, and complexes of Formulas (II) and (III) wherein Z is phenyl or naphthyl group preferably a phenyl group optionally substituted with up to three substituents preferably with up to two substituents selected from the group consisting of halogen, nitro, trihalomethyl, cyano, ($C_1$ to $C_4$) alkyl, ($C_1$ to $C_4$) alkoxy, ($C_1$ to $C_4$) alkylthio, ($C_1$ to $C_4$) alkylsulfinyl, ($C_1$ to $C_4$) alkylsulfonyl, phenoxy, phenylthio, phenylsulfinyl, phenylsulfonyl, and phenoxy, phenylthio, phenylsulfinyl or phenylsulfonyl substituted with up to two substituents selected from the group consisting of halogen, nitro, trifluoromethyl, cyano, methyl, methoxy, methylthio, methylsulfinyl and methylsulfonyl; $R^1$ is hydrogen; $R^2$ is selected from the group consisting of ($C_1$ to $C_{12}$) alkyl, ($C_5$ to $C_7$) cycloalkyl, ($C_2$ to $C_4$) alkenyl, ($C_5$ to $C_6$) cycloalkenyl, ($C_2$ to $C_4$) alkynyl, unsubstituted phenyl, benzyl or phenethyl or phenyl, benzyl or phenethyl, the aromatic portion of which is substituted with up to two halogen atoms; or $R^1$ and $R^2$ are taken together with the carbon atom to which they are attached to form a ($C_4$ to $C_7$) cycloalkyl group; Q is an unsubstituted 1 or 4-triazole; m is zero; and n is the integer 1.

A more preferred embodiment of this invention is the compounds, salts and complexes of Formulas (II) and (III) wherein Z is phenyl optionally substituted with up to three substituents preferably with up to two substituents selected from the group consisting of chlorine, bromine, methyl, methoxy, nitro, methylthio phenoxy, phenylthio, phenylsulfinyl and phenylsulfonyl; $R^1$ is hydrogen; $R^2$ is ($C_1$ to $C_{12}$) alkyl, cyclohexyl, allyl, cyclohexenyl, propargyl, phenyl, benzyl or phenethyl or monochloro substituted phenyl, benzyl or phenethyl; or $R^1$ and $R^2$ are taken together with the carbon atom to which they are attached to form a cyclopentyl group; Q is an unsubstituted 1 or 4-triazole; m is zero; and n is the integer 1.

Typical compounds encompassed by the present invention include:

1-[β-(2,4-dibromophenyl)hexyl]-1,2,4-triazole
4-[β-(2,5-dinitrophenyl)octyl]-1,2,4-triazole
1-[β-(4-phenoxyphenyl)hexyl]-1,2,4-triazole
4-[β-(2-phenylthiophenyl)propyl]-1,2,4-triazole
1-[β-(4-phenylsulfinylphenyl)octyl]-1,2,4-triazole
4-[β-(4-phenylsulfonylphenyl)pentyl]-1,2,4-triazole
1-[γ-(2-chlorophenylthiophenyl)hexyl]-1,2,4-triazole
4-[δ-(3-bromophenylsulfinylphenyl)decyl]-1,2,4-triazole
1-[δ-(4-methylsulfonylphenylsulfonylphenyl)tridecyl]-1,2,4-triazole
4-[γ-(2-methyl-4-methoxyphenylthiophenyl)pentadecyl]-1,2,4-triazole
1-[β-(3,5-diiodophenylsulfinylphenyl)hexadecyl]-1,2,4-triazole
4-[β-(3-chloro-4-methylphenylsulfonylphenyl)hexyl]-1,2,4-triazole
1-[γ-(3,5-ditrifluoromethylphenyl)nonyl]-1,2,4-triazole
4-[δ-(2,4,6-trichlorophenyl)dodecyl]-1,2,4-triazole
1-[β-(2,4,5-trimethylphenyl)tetradecyl]-1,2,4-triazole
4-[β-(2,4-dimethoxyphenyl)hexyl]3-methyl-1,2,4-triazole
1-[β-(2,4-dimethylthiophenyl)hexyl]5-chloro-1,2,4-triazole
4-[β-(3-iodophenyl)decyl]-1,2,4-triazole
1-[β-(2,6-dichlorophenyl)pentyl]-1,2,4-triazole
4-[β-(3,5-diethylphenyl)buten-2-yl]-1,2,4-triazole
4-[β-(4-cyanophenyl)β-phenylpropyl]-1,2,4-triazole
1-[γ-(2,4-dichlorobenzyl)heptyl]-1,2,4-triazole
4-[β-(2,4-difluorobenzyl)octyl]-1,2,4-triazole
1-[β-(2,4-dichlorophenethyl)hexyl]-1,2,4-triazole
4-[β-(4-iodophenyl)undecyl]-1,2,4-triazole
1-[δ-(2-methyl-4-chlorophenyl)dodecyl]-1,2,4-triazole
4-[δ-(2-methyl-4-methylthiophenyl)tridecyl]-1,2,4-triazole
1-[β-(4-tolyl)hexyl]-1,2,4-triazole
4-[β-(4-anisyl)hexyl]-1,2,4-triazole
4-[β-(2,4-dichlorophenyl)-β-cyclopropylethyl]-1,2,4-triazole
4-[β-(2,4-dichlorophenyl)-β-cyclopentylethyl]-1,2,4-triazole
1-[β-(2,4-dichloronaphthyl)hexyl]-1,2,4-triazole
4-[β-(2-fluoronaphthyl)hexyl]-1,2,4-triazole
1-[β-(2-nitronaphthyl)hexyl]-1,2,4-triazole
4-[β-(3,4-dichlorophenyl)octyl]-1,2,4-triazole
1-[β-(2,3-difluorophenyl)propyl]-1,2,4-triazole
4-[β-(2,5-diethylphenyl)tetradecyl]-1,2,4-triazole
1-[γ-(2,3,5-trichlorophenyl)hexyl]-1,2,4-triazole
4-[β-(4-trichloromethylphenyl)pentyl]-1,2,4-triazole
1-[β-(4-ethylsulfonylphenyl)hexyl]-5-cyano-1,2,4-triazole
4-[β-(2-bromo-4-nitrophenyl)hexyl]3-bromo-1,2,4-triazole
1-[β-(3-methylsulfinylphenyl)butyl]3-ethyl-1,2,4-triazole
4-[β-(2-methoxynaphthylethyl)hexyl]-1,2,4-triazole
1-[β-(2,4-dichlorophenyl)-4-chlorophenethyl]-1,2,4-triazole
4-[β-(4-benzylphenyl)-4-chlorophenethyl]-1,2,4-triazole
1-[γ-(3,5-dinitrophenyl)hexyl]-1,2,4-triazole and the agronomically acceptable acid addition salts and metal salt complexes thereof.

The 1 and 4-aralkyl-1,2,4-triazoles of the present invention can be prepared by standard general synthetic routes. A preferred method for preparing the 1-aralkyl-1,2,4-triazoles of this invention is as follows:

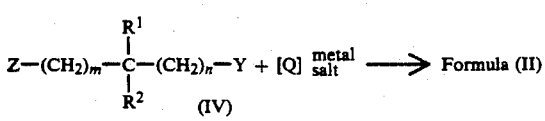

In this reaction sequence Z, $R^1$, $R^2$, Q, m and n are as defined in Formula (II); Y is halide, alkanesulfonate, arylsulfonate and the like and the metal salt of the 1-(1,2,4-triazole), Q, is preferably a sodium or potassium salt. This reaction can be run either neat or in an appropriate solvent such as benzene, toluene, xylene, glyme, N,N-dimethylformamide, dimethyl sulfoxide and the like, at temperatures from about 0° C. to about 150° C.

When the starting material of Formula (IV) is reacted with the 1H-1,2,4-triazole free base instead of its metal salt, at temperatures from about 50° C. to about 180° C., a mixture of 1-substituted and 4-substituted 1,2,4-triazoles is obtained and these triazoles can be easily separated by conventional chemical separation techniques such as extraction, chromatography, crystallization and the like.

A preferred method for preparing the 4-aralkyl-triazoles of this invention is as follows:

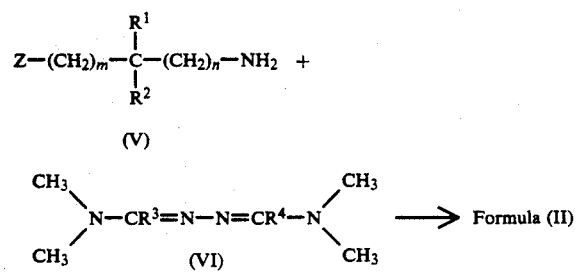

In this reaction sequence Z, $R^1$, $R^2$, m and n are as defined in Formula (II) and $R^3$ and $R^4$ are independently a hydrogen atom, a halogen atom, a ($C_1$ to $C_4$) alkyl group a nitro group or a cyano group. This reaction is run in an appropriate inert solvent such as benzene, toluene, xylene, and the like at temperatures from about 0° C. to about 150° C. with or without the presence of a suitable catalyst such as p-toluenesulfonic acid, benzene sulfonic acid, methanesulfonic acid and the like. Either reactant, i.e. Formula (V), or (VI) can be used in excess in this preparation and the mode of addition is not critical.

The starting materials of Formula (IV) can be prepared by standard synthetic methods. Examples of such preparative methods can be found in U.S. patent application Ser. No. 642,041 filed Dec. 8, 1975 by George A. Miller et al. which issued Aug. 8, 1978 as U.S. Pat. No. 4,105,762 and is assigned to a common assignee.

The starting materials of Formula (V) can be prepared by making the corresponding Formula (IV) starting materials wherein Y is chlorine, bromine and the like and reacting them with ammonia, either neat or in an appropriate solvent such as diethyl ether, tetrahydrofuran, methanol and the like at temperatures from about −40° C. to about 100° C.

The addition salts of the 1 & 4-aralkyl-1,2,4-triazoles of this invention can be prepared by standard techniques well-known in the art. For example, the 1 or 4-aralkyl-1,2,4-triazole of Formula (II) can be dissolved in an appropriate solvent such as diethyl ether, tetrahydrofuran, ethanol, methanol, and the like and treated with an equivalent or excess amount of a mineral or organic acid which may or may not be dissolved in an appropriate solvent. The mixture is then either cooled or evaporated to give the salt which can either be used as such or recrystallized from an appropriate solvent or combination of appropriate solvents.

The metal salt complexes of the above 1 & 4 substituted aralkyl-1,2,4-triazoles can be prepared by adding dropwise, with stirring, a stoichiometric amount of a metal salt dissolved in an appropriate solvent to a solution of the 1 & 4-substituted aralkyl-1,2,4-triazole of Formula (II) dissolved in a similarly appropriate solvent. The reaction mixture is briefly stirred and the solvent is removed under reduced pressure to give the metal salt complex of the respective 1 & 4-substituted aralkyl-1,2,4-triazole of Formula (III).

The metal salt complexes can also be prepared by mixing stoichiometric or excess amounts of the metal salt and 1 & 4-substituted aralkyl-1,2,4-triazole of Formula (II) in the desired amount of solvent containing the appropriate adjuvants just prior to spraying the plants. Adjuvants that may be included in this "in-situ" preparation may be detergents, emulsifiers, wetting agents, spreading agents, dispersing agents, stickers, adhesives, and the like which are used in agricultural applications.

Solvents that can be utilized in these procedures include any polar solvent e.g., water, methanol, ethanol, isopropanol or ethylene glycol and any aprotic dipolar solvent e.g., dimethylsulfoxide, acetonitrile, dimethylformamide, nitromethane or acetone.

The metal salt cations that may be used in these procedures can be selected from the group consisting of calcium, magnesium, manganese, copper, nickel, zinc, iron, cobalt, tin, cadmium, mercury, chromium, lead, barium, and the like.

Any appropriate anion e.g., chloride, bromide, iodide, sulfate, bisulfate, phosphate, nitrate, perchlorate, carbonate, bicarbonate, hydrosulfide, hydroxide, acetate, oxalate, malate, citrate and the like may be utilized as the counterion in the metal salt.

Any metal containing fungicides can also act as safening agents when used in place of metal salts. Typical metal containing fungicides that can be utilized in these procedures are: a) dithiocarbamates and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb); b) copper-based fungicides such as cuprous oxide, copper naphthenate, and Bordeaux mixture; and c) miscellaneous fungicides such as: phenylmercuric acetate, N-ethylmercuri-1,2,3,6-tetrahydro-3,6-endomethano-3,4,5,6,7,7-hexachlorophthalmide, phenylmercuri monoethanolammonium lactate, nickel-containing compounds and calcium cyanamide.

The compounds of this invention, except for those wherein $R^1$ and $R^2$ are both equal to hydrogen, possess an asymmetric carbon atom and thus exist as racemic mixtures. The d and l enantiomorphs in these racemic mixtures can be separated via standard techniques such as fractional crystallization with d-tartaric acid, l-tartaric acid, l-quinic acid and the like followed by basification and extraction of the d or l enantiomorph free base.

The following examples are provided merely to illustrate the methods of preparation of the compounds of the present invention. These examples are not meant to be considered, in any way, as limitations of the breadth and scope of the present invention. The temperatures expressed in these examples are in degrees Centigrade.

EXAMPLE 1

Preparation of
4-[2-(2,4-dichlorophenyl)hexyl]-1,2,4-triazole

A. 2-(2,4-Dichlorophenyl)hexyl amine

To a suspension of 9.0 g (0.24 mole) of lithium aluminum hydride in 200 ml of anhydrous ether is added 57 g (0.24 m) of α-n-butyl-2,4-dichlorobenzyl cyanide dropwise at 10°. The reaction mixture is stirred at room temperature for 30 minutes and at 35° overnight. Excess lithium aluminum hydride is then decomposed by addition of saturated ammonium chloride solution (50 ml), followed by 20% hydrochloric acid (300 ml) at 0°. The acidic aqueous layer is separated and extracted with ether. The combined ether portions are washed with water and dried over $MgSO_4$. When ether is evaporated under vacuo, there is obtained 63 g of a yellow solid. The solid is then dissolved in 20% sodium hydroxide solution and extracted with ether. The combined ether extracts are dried over $MgSO_4$. Solvent is evaporated to give 48 g of an oil. Vacuum distillation (101°–104°/0.1 mm) gives 38.3 g of pure product.

B. 4-[2-(2,4-dichlorophenyl)hexyl]-1,2,4-triazole

A mixture of 10 g (0.04 mole) of 2-(2,4-dichlorophenyl)hexyl amine, 5.7 g (0.04 mole) of N,N-dimethyl formamide azine and 0.5 g of p-toluene sulfonic acid in 100 ml of dry toluene is heated under reflux for 16 hours. The solvent is evaporated to give 15 g of a white solid which can be further purified by recrystallization from benzene to give 7.5 g of pure product.

nmr ($CDCl_3$): δ0.8–2.0 (complex multiplets, 9H), 3.8 (m, 1H), 4.3 (d, 2H), 7.3 (m, 3H), 8.0 (s, 2H)

EXAMPLE 2

Preparation of
1-[2-(2,4-dichlorophenyl)hexyl]-1,2,4-triazole and
4-[2-(2,4-dichlorophenyl)hexyl]-1,2,4-triazole A. 2-(2,4-Dichlorophenyl)hexyl methane sulfonate For the preparation of this compound see Example 4 below.

B. 1-[2-(2,4-dichlorophenyl)hexyl]-1,2,4-triazole and 4-[2-(2,4-dichlorophenyl)hexyl]-1,2,4-triazole A mixture of 8 g (0.025 mole) of 2-(2,4-dichlorophenyl)hexyl methane sulfonate and 6 g (0.087 mole) of 1H-1,2,4-triazole is mixed and heated at 120° for 4 hours. The reaction is poured into water and extracted with ether. The combined ether extracts are washed with water and dried over $MgSO_4$. The drying agent is filtered and to the filtrate is added conc. nitric acid dropwise until no more precipitate forms. Solvent is then decanted and the residue is washed with ether and back neutralized with dilute $NH_4OH$ solution to give 3 g of an oil. Analysis by glc and nmr reveals that this product contains a mixture of 1-[2-(2,4-dichlorophenyl)hexyl]-1,2,4-triazole and 4-[2-(2,4-dichlorophenyl)hexyl]-1,2,4-triazole in a ratio of 2:1.

nmr ($CDCl_3$): δ0.7–2.0 (m, 9H), 3.6–4.0 (m, 1H), 4.2–4.9 (m, 2H), 7.0–7.5 (m, 3H), and singlets at 7.8, 7.9 and 8.0 integrated for 2H

EXAMPLE 3

Preparation of
1-[2-(2,4-dichlorophenyl)hexyl]-1,2,4-triazole

The free base of 1-[2-(2,4-dichlorophenyl)hexyl]-1,2,4-triazole is obtained when the nitrate salt of Example 4 is back neutralized with 10% ammonium hydroxide solution.

nmr ($CDCl_3$): 0.7–2.0 (complex multiplets, 9H), 3.9 (m, 1H), 4.4 (d, 2H), 7.0–7.5 (m, 3H), 7.8 (s, 1H), 7.95 (s, 1H)

EXAMPLE 4

Preparation of
1-[2-(2,4-dichlorophenyl)hexyl]-1,2,4-triazolium nitrate

A. 2-(2,4-Dichlorophenyl)hexyl methane sulfonate

To 24.7 g (0.1 mole) of the 2-(2,4-dichlorophenyl)-hexan-1-ol and 13.8 g (0.12 mole) of methane sulfonyl chloride in 200 ml of benzene at 10° is slowly added 14.2 g (0.14 mole) of triethylamine. When the addition is complete the reaction is stirred and allowed to come up to ambient temperature over ½ hour period. The reaction slurry is then heated to reflux for ½ hour, cooled and poured into water. The organic solution is washed with dilute HCl then with water and finally with dilute sodium bicarbonate solution. After drying over anhydrous $MgSO_4$, the benzene is stripped off to give 31.8 g (98%) of the crude product. This material is identified by ir and nmr. The purity is determined by glc.

B. 1-[2-(2,4-dichlorophenyl)hexyl]-1,2,4-triazolium nitrate

To a dimethyl sulfoxide solution (25 ml) of sodium 1,2,4-triazole, generated from 2.2 g (0.032 mole) of 1H-1,2,4-triazole and 1.3 g (0.032 mole) of sodium hydroxide, is added 10 g (0.03 mole) of 2-(2,4-dichlorophenyl)hexyl methane sulfonate in 10 ml of dimethyl sulfoxide dropwise at 100°. The reaction is maintained at 100° for 1 hour and then poured into water and extracted with ether. The combined ether extracts are washed with water and dried over $MgSO_4$. Drying agent is then filtered and to the filtrate is added conc. nitric acid until no more precipitates form. The white precipitate (7.5 g) is filtered and is characterized as the nitric acid salt of the desired product.

nmr (DMSO): δ0.7–2.0 (complex multiplets, 9H), 3.9 (m, 1H), 4.7 (d, 2H), 7.5 (m, 3H), 8.5 (s, 1H), 9.0 (s, 1H), 9.3 (s, 1H)

EXAMPLE 7

Preparation of zinc chloride complex of
1-[2-(2,4-dimethylphenyl)hexyl]-1,2,4-triazole To 3.0 g (0.01166 mole) of 1-[2(2,4-dimethylphenyl)-hexyl]-1,2,4-triazole in 50 ml methanol is added 0.71 g (0.0052 mole) of zinc chloride and the mixture is allowed to stir for 15 minutes. The methanol is stripped to give 3.7 g of residue. The residue is triturated with hexane, and the solid which formed is filtered and dried to give 3.3 g (71.9%) of the product, mp 85°–6°.

EXAMPLE 10

Preparation of 1-(2-phenyltetradecyl)-1,2,4-triazole hydrochloride

To 6.6 g (0.09614 mole) of 1H-1,2,4-triazole in 50 ml of DMSO is added 3.8 g (0.0948 mole) of sodium hydroxide pellets and the mixture is stirred with warming until a solution formed. To this is added 25 ml of toluene and the reaction is heated to reflux and water is azeotroped from the reaction. When water azeotroping is complete, the toluene is stripped and the DMSO solution is cooled. To this solution is added 35.3 g (0.0958 mole) of 2-phenyltetradecyl methane sulfonate which has been prepared by the usual route. The reaction is then heated up to 130° for 20 hours and then cooled. To this solution is added 250 ml of water, and the organic material which separated is extracted with 2×200 ml of ether. The extract is dried over anhydrous magnesium sulfate, and is then treated with hydrogen chloride gas. The solid salt which precipitates is separated by filtration, washed with ether, and dried to give 16.9 g (46.7%) of the crude hydrochloride salt, mp 50°–3°. Five grams of the hydrochloride salt are recrystallized from ether/acetone to give 3.6 g of 1-(2-phenyltetradecyl)-1,2,4-triazolium chloride mp 82°–8°.

EXAMPLE 11

Preparation of 1-(2-phenyltetradecyl)-1,2,4-triazole

To 11.7 g of the crude hydrochloride salt from Example 10 above in 200 ml of water is added 4.0 g (0.05 mole) of 50% sodium hydroxide. The mixture is stirred for 15 minutes and then the organic soluble material is extracted into 2×200 ml of ether. The combined extracts are washed with 2×50 ml of water, dried over anhydrous magnesium sulfate, and concentrated to give 8.3 g (78.5%) of the oil product.

EXAMPLE 12

Preparation of
1-[β,β-tetramethylene-β-(2,4-dichlorophenyl)ethyl]-1,2,4-triazolium chloride A. αα-Tetramethylene-2-(2,4-dichlorophenyl)ethyl methane sulfonate 1. αα-tetramethylene-2,4-dichlorobenzyl cyanide Into a 500 ml three-necked flask is placed 200 ml of 25% sodium hydroxide solution and 4 g of tetraethylammonium bromide. To this suspension is added dropwise a solution of 33.5 g (0.2 mole) of 2,4-dichlorobenzyl cyanide and 43 g (0.2 mole) of 1,4-dibromobutane in 200 ml of methylene chloride under nitrogen. When the addition is over, the reaction mixture is heated to reflux for 1.5 hours. It is then poured into water and the layers are separated. The aqueous layer is extracted with 100 ml of methylene chloride. The combined organic extracts are washed with water, saturated sodium chloride solution and dried over magnesium sulfate. Solvent is evaporated to give a light yellow oil. Vacuum distillation (130°–140°/0.2 mm) gives 30.4 g (63%) of pure product, which is identified by nmr.

2. αα-tetramethylene-2,4-dichlorophenyl acetic acid

A mixture of 14 g (0.06 mole) of α, α-tetramethylene-2,4-dichlorobenzyl cyanide, 160 ml of 40% potassium hydroxide solution, and 120 ml of diethylene glycol is heated under reflux for 3 days. The reaction mixture is poured into water and extracted with ether. The aqueous layer is then made acidic with hydrochloric acid followed by extraction with ether. The combined ether extracts from the acidic solution are washed with water, saturated sodium chloride solution and then dried over magnesium sulfate. Solvent is evaporated to give 12.4 g of crude acid which is recrystallized from hexane/benzene to give 8 g of pure acid, m.p. 136°–138°.

3. 2,2-tetramethylene-2-(2,4-dichlorophenyl)-ethyl alcohol

To a suspension of 3 g (0.08 mole) of lithium aluminum hydride in 300 ml of anhydrous ether is added dropwise 13 g (0.05 mole) of α,α-tetramethylene-2,4-dichlorophenyl acetic acid in 50 ml of ether under nitrogen. The reaction mixture is then heated to reflux for one hour. Excess lithium aluminum hydride is carefully decomposed by dropwise addition of 10% hydrochloric acid into the reaction mixture. The two layers are separated and the aqueous layer is extracted with ether. The combined ether extracts are washed with water and dried over magnesium sulfate. Solvent is evaporated to give 9.8 g of alcohol, which is identified by nmr.

4. 2,2-tetramethylene-2-(2,4-dichlorophenyl)ethyl methane sulfonate

To a mixture of 9.8 g (0.04 mole) of 2,2-tetramethylene-2-(2,4-dichlorophenyl) ethyl alcohol and 5 g (.04 mole) of methane sulfonyl chloride in 30 ml of benzene is added dropwise 5 g (.05 mole) of triethyl amine. The reaction mixture is stirred at room temperature overnight. The precipitate formed is filtered. The benzene solution is washed with water then dilute hydrochloric acid and dried over magnesium sulfate. Solvent is evaporated to give 12 g of product, which is identified by nmr.

B. 1-[β,β-tetramethylene-β-(2,4-dichlorophenyl) ethyl]-1,2,4-triazolium chloride To a 0.65 g (0.009 mole) of 1H-1,2,4-triazole in 50 ml of DMSO is added 0.37 g (0.009 mole) of sodium hydroxide pellets and the mixture is stirred with heating (60°–90°) until a solution formed. To this solution is added 25 ml of toluene and the reaction is heated to reflux and the water formed is azeotroped from the reaction. When water azeotroping is complete, the toluene is stripped and the DMSO solution is cooled to 115°.

To this solution is added 3 g (0.009 mole) of 2,2-tetramethylene-2-(2,4-dichlorophenyl) ethyl methane sulfonate dissolved in 10 ml of DMSO dropwise. After the reaction is heated at 115° for 2 hours, it is poured into 150 ml of water and extracted with ether. The combined ether extracts are washed with water and dried over MgSO₄. Solvent is evaporated to give 2.5 g of crude product. This material is dissolved in 200 ml of ether and dry hydrogen chloride gas is bubbled through the ether solution. The solid formed is filtered and dried under vacuum to give 1.2 g of expected product, mp 175°–9°.

EXAMPLE 13

Preparation of
1-[2-(2-phenoxyphenyl)hexyl]-1,2,4-triazolium chloride

A. o-Phenoxybenzyl chloride

Into a 1 liter round bottom flask equipped with a stirrer, a condenser, a thermometer and an addition funnel are charged 25 g (0.125 mole) of o-phenoxybenzyl alcohol and 250 ml of benzene. Thionyl chloride (18.0 g, 0.15 mole) is added dropwise at room temperature. After the addition, the reaction mixture is heated to reflux for 2 hours. Solvent is then evaporated under vacuum to give 29 g of product.

B. α-n-Butyl o-phenoxybenzyl cyanide

Into a 300 ml three-necked flask equipped with a stirrer, a condenser, a thermometer and an addition funnel are charged 50 ml of dimethyl sulfoxide and 7.4 g (0.15 mole) of sodium cyanide. A solution of 30 g (0.14 mole) of o-phenoxybenzyl chloride in 10 ml of dimethyl sulfoxide is added dropwise at room temperature. The reaction mixture is stirred for 1½ hours. Butyl chloride (18.7 g, 0.14 mole) is then added to the reaction mixture followed by dropwise addition of 34.3 g (0.43 mole) of 50% sodium hydroxide solution. Reaction temperature increased to 52° after the addition and stirring is continued for 1 hour. The reaction mixture is then diluted with 150 ml of water and extracted with hexane. The combined hexane extracts are washed with water and dried over $MgSO_4$. Solvent is evaporated to give 32 g of product. The product can be further purified by vacuum distillation (b.p. 137–142/0.2 mm).

C. n-Butyl-2-(o-phenoxyphenyl)hexanoate

Into a 500-ml round bottom flask are placed 77.7 g (1 mole) of n-butanol, 36.5 g (0.14 mole) of δ-n-butyl o-phenoxybenzyl cyanide and 14.4 g (0.45 mole) of conc. sulfuric acid. The mixture is heated to reflux overnight. It is then cooled, poured into water and extracted with toluene. The combined extracts are washed with water and dried over $MgSO_4$. Solvent is evaporated to give 50 g of product.

D. 2-(o-phenoxyphenyl)hexan-1-ol

Into a 500-ml three-necked round bottom flask equipped with a stirrer, a condenser fitted with a drying tube, a thermometer and an addition funnel are placed 1.8 g (0.047 mole) of lithium aluminum hydride and 50 ml of anhydrous ether. To this slurry is added 20.7 g (0.05 mole) of n-butyl-2-(o-phenoxyphenyl) hexanoate in 50 ml of ether dropwise at 10°. The reaction mixture is stirred for 2 hours at room temperature, poured into ice water and acidified with dilute hydrochloric acid. The mixture is then extracted with ether and the combined ether extracts are washed with water and dried over $MgSO_4$. Solvent is evaporated to give 17.5 g of crude product. Vacuum distillation (138°–145°/0.25 mm) gives 16.1 g of pure product.

E. 2-(o-phenoxyphenyl)hexyl methane sulfonate:

Into a 500 ml round bottom flask are placed 15.6 g (0.06 mole) of 2-(o-phenoxyphenyl)hexan-1-ol, in 100 ml of benzene and 7.9 g. (0.07 mole) of methane sulfonyl chloride. To this mixture is added 8.2 g (0.08 mole) of triethyl amine dropwise at 10°. The reaction mixture is stirred overnight at room temperature and poured into 150 ml 10% hydrochloric acid. It is then extracted with benzene and the combined benzene extracts are washed with water and dried over $Na_2SO_4$. Solvent is evaporated to give 20 g of product.

F. 1-[2-(2-phenoxyphenyl)hexyl]-1,2,4-triazolium chloride:

To 2.0 g (0.03 mole) of 1H-2,2,4-triazole in 75 ml of dimethylsulfoxide is added 1.2 g (0.03 mole) of sodium hydroxide pellets and the mixture is stirred with heating (60°–90°) until a solution forms. To this solution is added 37 ml of xylene and the reaction is heated to reflux and the water formed is azeotroped from the reaction. When water azeotroping is complete, the xylene is stripped and the dimethylsulfoxide solution is cooled to 115°.

To this solution is added dropwise 10.0 g (0.29 mole) of 2-(o-phenoxyphenyl)hexyl methane sulfonate dissolved in 10 ml of dimethylsulfoxide. After the reaction is heated at 125° overnight, it is poured into 150 ml of water and extracted with ether. The combined ether extracts are washed with water and dried over sodium sulfate. Solvent is evaporated to give 8.0 g of crude product. This material is redissolved in 200 ml of ether and dry hydrogen chloride gas is bubbled through the ether solution. The solid formed is filtered and dried under vacuum to give 5.6 g of expected product, m.p. 142°–6°.

Table I and II below give the structure and elemental analysis of some of the more preferred compounds encompassed by the present invention.

TABLE I $$Z-\underset{\underset{R^2}{|}}{\overset{\overset{R^1}{|}}{C}}-CH_2-Q.M$$

| | Z | $R^1$ | $R^2$ | Q | M |
|---|---|---|---|---|---|
| 1 | $2,4Cl_2-C_6H_3$ | $C_4H_{9n}$ | H | 4-triazole | — |
| 2 | $2,4Cl_2-C_6H_3$ | $C_4H_{9n}$ | H | 1 & 4-triazole | — |
| 3 | $2,4Cl_2-C_6H_3$ | $C_4H_{9n}$ | H | 1-triazole | — |
| 4 | $2,4Cl_2-C_6H_3$ | $C_4H_{9n}$ | H | 1-triazole | $HNO_3$ |
| 5 | $2,4(CH_3)_2-C_6H_3$ | $C_4H_{9n}$ | H | 1-triazole | HCl |
| 6 | $2,4(CH_3)_2-C_6H_3$ | $C_4H_{9n}$ | H | 1-triazole | — |
| 7 | $2,4(CH_3)_2-C_6H_3$ | $C_4H_{9n}$ | H | 1-triazole | ½$ZnCl_2$ |
| 8 | $2,4,6-(CH_3)_3C_6H_2$ | $CH_3$ | H | 1-triazole | HCl |
| 9 | $2,4,6-(CH_3)_3C_6H_2$ | $CH_3$ | H | 1-triazole | — |
| 10 | $C_6H_5$ | $C_{12}H_{25}$ | H | 1-triazole | HCl |
| 11 | $C_6H_5$ | $C_{12}H_{25}$ | H | 1-triazole | — |
| 12 | $2,4Cl_2-C_6H_3$ | $R^1 + R^2 =$ $-(CH_2)4-$ | | H | 1-triazole | HCl |
| 13 | $2-C_6H_5O-C_6H_4$ | $C_4H_{9n}$ | H | 1-triazole | HCl |
| 14 | $3-C_6H_5O-C_6H_4$ | $C_4H_{9n}$ | H | 1-triazole | $HNO_3$ |

TABLE II

| Ex. No. | mp °C. | Elemental Analysis: Calc'd (Found) | | | | |
|---|---|---|---|---|---|---|
| | | C | H | Cl | N | O or Zn |
| 1 | 110–3 | 56.39 (56.55) | 5.75 (5.99) | 23.78 (23.38) | 14.09 (14.05) | |
| 2 | oil | 56.39 (55.11) | 5.75 (5.81) | 23.78 (23.89) | 14.09 (12.70) | |
| 3 | oil | 56.39 (56.19) | 5.75 (5.87) | 23.78 (23.95) | 14.09 (13.69) | |
| 4 | 108–10 | 46.55 (46.38) | 5.02 (5.01) | 19.64 (19.67) | 15.51 (15.22) | 13.29 (13.39) |
| 5 | 145–51 | 65.40 (65.66) | 8.23 (8.37) | 12.07 (11.76) | 14.30 (14.47) | |
| 6 | oil | 74.67 (74.51) | 9.00 (9.19) | — — | 16.33 (16.49) | |
| 7 | 85–6 | 59.03 (58.72) | 7.12 (7.14) | 10.89 (10.56) | 12.09 (13.16) | 10.04 (10.47) |
| 8 | 180–7 | 63.26 (62.75) | 7.59 (7.42) | 13.34 (13.16) | 15.81 (15.90) | |
| 9 | oil | 73.32 (72.00) | 8.35 (8.05) | — — | 18.33 (18.33) | |
| 10 | 82–8 | 69.90 (69.34) | 9.60 (9.52) | 9.38 (8.83) | 11.12 (10.89) | |
| 11 | oil | 77.37 (77.32) | 10.33 (10.37) | — | 12.30 (12.06) | |
| 12 | 175–9 | 50.55 (50.19) | 4.85 (4.83) | 31.97 (29.20) | 12.63 (12.68) | |
| 13 | 142–146 | 67.12 (67.23) | 6.76 (6.79) | 9.91 (10.11) | 11.74 (12.07) | 4.47 (5.04) |
| 14 | 121–4 | 62.49 (61.11) | 6.29 (6.30) | | 14.57 (14.30) | 16.65 (17.28) |

The 1&4-aralkyl-1,2,4-triazoles, enantiomorphs, acid addition salts and metal salt complexes of this invention are broad-spectrum fungicides which possess a high degree of activity against assorted phytopathogenic fungi. These compounds, enantiomorphs, salts and complexes are particularly effective at rates of application from about 50 to about 2000 ppm in controlling barley net blotch (*Helminthosporium teres*) on barley plants, grey mold (*Botrytis cinerea*) on faba beans, bean powdery mildew (*Erysiphe polygoni*) on bean plants, grape downy mildew (*Plasmopora viticola*) on grape seedlings, rice blast (*Piricularia oryzae*) on rice plants, tomato late blight (*Phytophthora infestans*) on tomato seedlings, and wheat stem rust (*Puccinia graminis* f. sp. *tritici* race 15B-2) on wheat seedlings.

In evaluating these compounds, a preliminary fungicidal evaluation is carried out using the compounds at 300 ppm and spraying the plants to run off in a carrier volume of about 150 gallons/acre.

The general procedure is to take potted plants in proper condition of growth for susceptibility to the fungal disease to be evaluated, to spray these on a moving belt and allow them to dry. The proper plants are then inoculated with the fungal spores and then allowed to incubate until the disease has developed and the percent control is read or estimated.

The following test methods are employed in evaluating the fungicidal activity of the compounds, enantiomorphs, salts and complexes of this invention.

EXAMPLE A - Barley Net Blotch (*Helminthosporium teres*)

Barley plants (var. Wong) are trimmed to a height of approximately 2.5 inches, 24 hours prior to chemical application. This procedure provides plants of a uniform height and permits rapid inoculation of treated plants. The barley plants are inoculated by spraying the foliage of the plants with a hand sprayer until small droplets of the inoculum are observed on the leaves. Inoculated plants are incubated in a humid environment at 75°-80° F. for 24 hours prior to being placed in the greenhouse at 70°-75° F. Treatment comparisons are made 6 to 7 days after inoculation. Typical barley net blotch symptoms initially appear as irregular sunken water-soaked areas which become necrotic as the lesions enlarge. Certain of the 1&4-aralkyl-1,2,4-triazoles of this invention demonstrate complete control over *Helminthosporium teres* at application rates of 300 ppm.

EXAMPLE B - Broad Bean Gray Mold Leaf Spot (*Botrytis cinerea*)

Broad bean plants (var. Vicia faba) are trimmed to a height of approximately 4.5 inches, 24 hours prior to chemical application. This procedure provides plants of a uniform height and permits rapid and uniform inoculation of the treated plants. Broad bean plants are inoculated by spraying the foliage with a herbicide belt sprayer. Inoculated plants are incubated in a humid environment at 75°-80° F. for 66 hours. Treatment comparisons are made 66 to 68 hours after inoculation. Typical broad bean gray mold leaf spot symptoms appear as regular circular to lanceolate lesions on plant leaves and stems. Certain of the 1&4-aralkyl-(1,2,4-triazoles) of this invention demonstrate greater than 70% control over *Botrytis cinerea* at application rates of 300 ppm.

EXAMPLE C-Bean Powdery Mildew (*Erysiphe polygoni*)

Bean plants (var. Drawf Hort) are thinned to two plants per pot 24 hours prior to chemical application. Bean plants are inoculated by spraying the leaves and stems with inoculum until a uniform film of inoculum is observed on the plant. Inoculated plants are maintained under existing greenhouse conditions. Treatment comparisons are made 8 to 10 days after inoculation. Typical bean powdery mildew symptoms are circular white mycelial mats (fructifications) on the leaf surface. Certain of the 1&4-aralkyl-(1,2,4-triazoles) of this invention demonstrate complete control over *Erysiphe polygoni* at application rates greater than 300 ppm.

EXAMPLE D-Grape Downy Mildew (*Plasmopora viticola*)

Grape seedlings (var. Siebel 1000) 4 to 5 inches tall are used. *Plasmopora viticola* is cultured on grape leaves for 7 days at 65°-75° F. The grape plants are inoculated by spraying the leaves with a hand held air brush until small uniform droplets of inoculum are observed on the leaves. The inoculated plants are incubated in a humid environment at 65°-70° F. for 48 hours prior to being placed in a growth room. Typical grape downy mildew symptoms appear on the upper surface as pale-yellow spots variable in size and form, frequently circular without a distinct line of demarcation. Under humid conditions the lower leaf surface is covered by conspicuous fungal growth. Certain of the 4-aralkyl-(1,2,4-triazoles) of this invention possess greater than 90% control over *Plasmopora viticola* at application rates of 300 ppm.

EXAMPLE E-Rice Blast (*Piricularia oryzae*)

Rice plants (var. Nova 66) are trimmed to a height of approximately 5 inches, 24 hours prior to chemical application. This procedure provides plants of uniform height and permits rapid inoculation of treated plants. Rice plants are inoculated by spraying the leaves and stems with an air brush until a uniform film of inoculum is observed on the leaves. The inoculated plants are incubated in a humid environment (75°-85° F.) for 24 hours prior to being placed in a greenhouse environment. Treatment comparisons are made 7 to 8 days after inoculation. Initial rice blast lesions appear as small brown necrotic spots on the foliage. The typical lesion is ecliptical, 1 to 2 cm. long with a large necrotic gray center and brown margins. Certain of the 1-aralkyl-(1,2,4-triazoles) of this invention possess complete control over *Piricularia oryzae* at application rates of 300 ppm.

EXAMPLE F-Tomato Late Blight (*Phytophthora infestans*)

Tomato (var. Rutgers) seedlings, 2.5 to 3 inches tall, are fertilized with a water soluble fertilizer 4 to 5 days prior to chemical application to promote rapid succulent growth and better symptom expression. The spore suspension is applied with a DeVilbiss atomizer at 8 to 10 psi. air pressure onto the leaf undersurface until fine droplets are formed. Inoculated seedlings are placed in a humid environment at 60°-62° F. for 40 to 45 hours, prior to being placed in the greenhouse at 70°-75° F. Treatment comparisons are made 5 to 6 days after inoculation. Initially, typical tomato late blight symptoms appear as irregular, greenish-black, water-soaked patches which enlarge and become brown, with a firm corrugated surface. Severe infection will resemble frost damage. Certain of the 1-aralkyl-(1,2,4-triazoles) of the present invention possess complete control over *Phytophthora infestans* at application rates of 300 ppm.

EXAMPLE G-Wheat Stem Rust (*Puccinia graminis* f. sp. *tritici* race 15B-2)

Seven-day-old wheat plants (var. Monon) are trimmed to approximately 2.5 inches, 24 hours prior to chemical application to provide a uniform plant height and to facilitate uniform inoculation. Wheat stem rust is cultured on wheat seedlings (var. Monon) for a period of 14 days under existing greenhouse conditions. Wheat plants are inoculated by applying the stem rust spore suspension, until run-off, with a DeVilbiss atomizer at 5 psi. air pressure. After inoculation, the plants are placed into a humid environment at approximately 68° F. A timer is used to permit 12 hours of continuous darkness followed by a minimum of 3 to 4 hours of light with an intensity of 500 foot candles. The temperature in the chamber should not exceed 85° F. At the end of the light period, the fogger is turned off and vented to allow the plants to dry slowly prior to being placed into a greenhouse environment. The plants are permitted to grow under greenhouse conditions for a period of 2 weeks prior to making treatment comparisons. Wheat stem rust is characterized by brick red spores in irregularly shaped sori on the leaves and stems of the wheat seedlings. Certain of the 1&4-aralkyl-(1,2,4-triazoles) of the present invention possess complete control over *Puccinia graminis* f. sp. *tritici* race 15B-2 at application rates of 300 ppm.

The 1&4-aralkyl-1,2,4-triazoles, enantimorphs, acid addition salts and metal salt complexes of the present invention are useful as agricultural fungicides and as such can be applied to various loci such as the seed, the soil or the foliage. For such purposes these compounds can be used in the technical or pure form as prepared, as solutions or as formulations. The compounds are usually taken up in a carrier or are formulated so as to render them suitable for subsequent dissemination as fungicides. For example, these chemical agents can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art can be found in the John W. McCutcheon, Inc. publication "Detergents and Emulsifiers, Annual."

In general, the compounds of this invention can be dissolved in certain solvents such as acetone, methanol, ethanol, dimethylformamide, pyridine or dimethyl sulfoxide and such solutions can be extended with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent which permits dispersion of the fungicide in water. The concentration of the active ingredient in emulsifiable concentrates is usually from about 10% to about 90% and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of from about 20% to about 98%, preferably from about 40% to about 75%. A typical wettable powder is made by blending 50 parts of 1-[β-(2,4-dichlorophenyl)hexyl] 1,2,4-triazole, 45 parts of a synthetic precipitated hydrated silicon dioxide sold under the trademark Hi-Sil®, and 5 parts of sodium lignosulfonate. In another preparation a kaolin type (Barden) clay is used in place of the Hi-Sil in the above wettable powder, and in another such preparation 25% of the Hi-Sil is replaced with a synthetic sodium silico aluminate sold under the trademark Zeolex®7.

Dusts are prepared by mixing the 1&4-aralkyl-1,2,4-triazoles, enantiomorphs, salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to from about 1% to about 10% use concentration.

The 1&4-aralkyl-1,2,4-triazoles, enantiomorphs, salts and complexes thereof can be applied as fungicidal sprays by methods commonly employed, such as conventional high-gallonage hydraulic sprays, low-gallonage sprays, air-blast blast spray, aerial sprays and dusts. The dilution and rate of application will depend upon the type of equipment employed, the method of application and diseases to be controlled, but the preferred effective amount is usually from about 0.1 lb. to about 50 lbs. per acre of the active ingredient.

As a seed protectant, the amount of toxicant coated on the seed is usually at a dosage rate of from about 0.1 to about 20 ounces per hundred pounds of seed. As a soil fungicide the chemical can be incorporated in the soil or applied to the surface usually at a rate of from about 0.1 to about 50 lbs. per acre. As a foliar fungicide, the toxicant is usually applied to growing plants at a rate of from about 0.25 to about 10 lbs. per acre.

Fungicides which can be combined with the fungicides of this invention includes:

(a) dithiocarbamate and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb), zinc propylenebisdithiocarbamate (propineb), sodium methyldithiocarbamate (methan), tetramethylthiuram disulfide (thiram), the complex of zineb and polyethylene thiuram disulfide, 3,5-dimethyl-1,3,5-2H-tetrahydrothiadiazine-2-thione (dazomet); and mixtures of these and mixtures with copper salts;

(b) nitrophenol derivatives such as: dinitro-(1-methylheptyl) phenyl crotonate (dinocap), 2-sec-butyl-4,6-dinitrophenyl 3,3-dimethylacrylate (binapacryl), and 2-sec-butyl-4,6-dinitrophenyl isopropyl carbonate;

(c) heterocyclic structures such as: N-trichloromethylthiotetrahydrophthalimide (captan), N-trichloromethylthiophthalimide (folpet), 2-heptadecyl-2-imidazole acetate (glyodine), 2-octylisothiazol-3-one, 2,4-dichloro-6-(o-chloroanilino)-s-triazine, diethyl phthalimidophosphorothioate, 4-butyl-1,2,4-triazole, 5-amino-1-[bis(dimethylamino)-phosphinyl]-3-phenyl-1,2,4-triazole, 5-ethoxy-3-trichloromethyl-1,2,4-thiadiazole, 2,3-dicyano-1,4-dithiaanthraquinone (dithianon), 2-thio-1,3-dithio-[4,5-b]quinoxaline (thioquinox), methyl 1-(butylcarbamoyl)-2-benzimidazole carbamate (benomyl), 2-(4'-thiazolyl) benzimidazole (thiabendazole), 4-(2-chlorophenylhydrazono)-3-methyl-5-isoxazolone, pyridine-2-thiol-1-oxide, 8-hydroxyquinoline sulfate and metal salts thereof; 2,3-dihydro-5-carboxanilido-6-methyl-1,4-oxathiin-4,4-dioxide, 2,3-dihydro-5-carboxanilido-6-methyl-1,4-oxathiin, α-(phenyl)-α-(2,4-dichlorophenyl)-5-pyrimidinyl-methanol (triarimol), cis-N-[(1,1,2,2-tetrachloroethyl)thio]-4-cyclohexene-1,2-dicarboxyimide, 3-[2-(3,5-dimethyl-2-oxycyclohexyl-2-hydroxy]-glutarimide (cycloheximide), dehydroacetic acid, N-(1,1,2,2-tetrachloroethylthio)-3a,4,7,7a-tetrahydrophthalimide (captafol), 5-butyl-2-ethylamino-4-hydroxy-6-methylpyrimidine (ethirimol), acetate of 4-cyclododecyl-2,6-dimethylmorpholine (dodemorph), and 6-methyl-2-oxo-1,3-dithiolo[4,5-b]-quinoxaline (quinomethionate).

(d) miscellaneous halogenated fungicides such as: tetrachloro-p-benzoquinone (chloranil), 2,3-dichloro-1,4-naphthoquinone (dichlone), 1,4-dichloro-2,5-dimethoxybenzene (chloroneb), 3,5,6-trichloro-o-anisic acid (tricamba), 2,4,5,6-tetrachloroisophthalonitrile (TCPN), 2,6-dichloro-4-nitroaniline (dichloran), 2-chloro-1-nitropropane, polychloronitrobenzenes such as: pentachloronitrobenzene (PCNB) and tetrafluorodichloroacetone;

(e) fungicidal antibiotics such as: griseofulvin, kasugamycin and streptomycin;

(f) copper-based fungicides such as: cuprous oxide, basic cupric chloride, basic copper carbonate, copper naphthenate, and Bordeaux mixture; and (g) miscellaneous fungicides such as: diphenyl, dodecylguanidine acetate (dodine), phenylmercuric acetate, N-ethylmercuri-1,2,3,6-tetrahydro-3,6-endomethano-3,4,5,6,7,7-hexachlorophthalimide, phenylmercuric monoethanol ammonium lactate, p-dimethylaminobenzenediazo sodium sulfonate, methyl isothiocyanate, 1-thiocyano-2,4-dinitrobenzene, 1-phenylthiosemicarbazide, nickel-containing compounds, calcium cyanamide, lime sulfur, sulfur, and 1,2-bis(3-methoxycarbonyl-2-thioureido) benzene (thiophanatemethyl).

The 1 & 4-aralkyl-1,2,4-triazoles, enantiomorphs, addition salts and metal salt complexes of this invention can be advantageously employed in various ways. Since these compounds possess broad spectrum fungicidal activity, they can be employed in the storage of cereal grain. These complexes can also be employed as fungicides in turf, fruit orchards, vegetables and golf course applications. Other applications of the 1 & 4-aralkyl-1,2,4-triazoles of this invention will suggest themselves to those skilled in the art of agriculture and horticulture.

We claim:

1. A compound of the formula

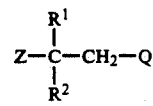

wherein

Z is phenyl or phenyl substituted with up to two halogen substituents;

$R^1$ is hydrogen;

$R^2$ is ($C_1$–$C_{12}$)alkyl, phenyl, benzyl, phenethyl, or phenyl, benzyl or phenethyl substituted with up to two halogen substituents; and Q is 1-(1,2,4-triazolyl); and the agronomically acceptable enantiomorphs, acid addition salts and metal salt complexes.

2. The compound of claim 1 wherein Z is phenyl or phenyl substituted with two chlorine substituents; and $R^2$ is ($C_3$–$C_5$)-alkyl, phenyl, benzyl, phenethyl or phenyl, benzyl or phenethyl substituted with two chlorine substituents.

3. The compound of claim 2 wherein $R^2$ is ($C_3$–$C_5$)alkyl.

4. The compound of claim 3 wherein Z is phenyl or 2,4-dichlorophenyl; and $R^2$ is ($C_3$–$C_5$)alkyl, phenyl, benzyl, phenethyl, 2,4-dichlorophenyl, 2,4-dichlorobenzyl or 2,4-dichlorophenethyl.

5. A compound of the formula

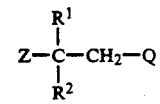

wherein

Z is 2,4-dichlorophenyl;

$R^1$ is hydrogen;

$R^2$ is ($C_3$–$C_5$)alkyl, phenyl, benzyl or phenethyl; and

Q is 1-(1,2,4-triazolyl);

and the agronomically acceptable enantiomorphs, acid addition salts and metal salt complexes.

6. The compound of claim 5 wherein $R^2$ is ($C_3$–$C_5$)alkyl or benzyl.

7. The compound of claim 5 wherein Z is 2,4-dichlorophenyl; and $R^2$ is n-$C_4H_9$.

8. A compound of the formula

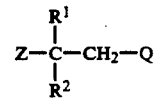

wherein

Z is phenyl or phenyl substituted with up to two chlorine substituents;

$R^1$ is hydrogen;

$R^2$ is ($C_1$–$C_{12}$)alkyl; and

Q is 1-(1,2,4-triazolyl);

and the agronomically acceptable enantiomorphs, acid addition salts and metal salt complexes.

9. The compound of claim 8 wherein $R^2$ is dodecyl.

10. The compound of claim 2 wherein Z is a dichlorophenyl and $R^2$ is benzyl.

11. A compound of the formula

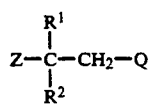

wherein
Z is unsubstituted phenyl or phenyl substituted with up to two substituents selected from the group consisting of halogen;
$R^1$ is hydrogen;
$R^2$ is selected from the group consisting of $(C_1-C_{12})$alkyl, $(C_5-C_6)$cycloalkenyl, $(C_2-C_4)$alkynyl, unsubstituted phenyl, benzyl or phenethyl or phenyl, benzyl or phenethyl substituted with up to two substituents selected from the group consisting of halogen, nitro, trifluoromethyl and cyano; or
$R^1$ and $R^2$ are taken together to form $(C_4-C_7)$cycloalkyl; and
Q is 1-(1,2,4-triazolyl) optionally substituted with up to two substituents selected from the group consisting of halogen, $(C_1-C_4)$alkyl, nitro and cyano; and the agronomically acceptable enantiomorphs, acid addition salts and metal salt complexes.

12. The compound of claim 11 wherein Z is phenyl or phenyl substituted with up to two halogen substituents; $R^2$ is $(C_3-C_5)$alkyl, phenyl, benzyl, phenethyl or monochloro substituted phenyl, benzyl or phenethyl; and Q is 1-(1,2,4-triazole).

13. The compound of claim 12 wherein Z is phenyl or phenyl substituted with up to two chlorines, $R^2$ is $(C_3-C_5)$alkyl, phenyl, benzyl or monochloro substituted phenyl or benzyl.

14. A fungicidal composition for controlling phytopathogenic fungi which comprises an agronomically acceptable carrier and, as the active ingredient, a fungicidally-effective amount of a compound of claim 11.

15. A fungicidal composition for controlling phytopathogenic fungi which comprises an agronomically acceptable carrier and, as the active ingredient, a fungicidally-effective amount of a compound of claim 7.

16. A method for controlling phytopathogenic fungi which comprises applying to a plant, to plant seed or to the plant habitat, a fungicidally effective amount of a compound according to claim 11.

17. A method for controlling phytopathogenic fungi which comprises applying to a plant, to plant seed or to the plant habitat, a fungicidally effective amount of a compound of claim 7.

18. The compound of claim 6 wherein $R^2$ is $(C_3-C_5)$alkyl.

19. The compound of claim 1 wherein Z is phenyl substituted with two halogen substituents; and $R^2$ is $(C_3-C_5)$alkyl, phenyl, benzyl or phenethyl.

20. The compound of claim 2 wherein Z is phenyl substituted with two chlorine substituents; and $R^2$ is $(C_3-C_5)$alkyl, phenyl, benzyl or phenethyl.

21. A chemical compound selected from the group consisting of 1H-1,2,4-triazole derivative having the formula:

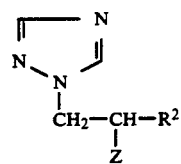

and the physiologically acceptable acid addition salts thereof, wherein:
Z is a member selected from the group consisting of mono-, di- and tri-halophenyl and
$R^2$ is a member selected from the group consisting of alkyl having from 1 to 10 carbon atoms, cycloalkyl, lower alkenyl, and aryl-lower alkyl, said aryl being selected from the group consisting of phenyl, and substituted phenyl, wherein said substituted phenyl is phenyl having from 1 to 3 substituents independently selected from the group consisting of halo, lower alkyl, lower alkyloxy, cyano, nitro and phenyl provided that when more than 1 substituents are present only 1 thereof may be selected from the group consisting of cyano, nitro and phenyl.

22. A chemical compound according to claim 21 selected from the group consisting of 1-[2-(2,4-dibromophenyl)hexyl]-1H-1,2,4-triazole and the physiologically acceptable acid addition salts thereof.

23. A chemical compound according to claim 21 selected from the group consisting of 1H-1,2,4-triazole derivative having the formula:

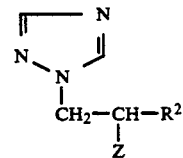

and the physiologically acceptable acid addition salts thereof, wherein:
Z' is selected from the group consisting of dichlorophenyl and dibromophenyl; and
$R^2$ is selected from the group consisting of alkyl having from 1 to 8 carbon atoms, cycloalkyl and -($C_2$ to $C_4$)alkenyl-.

24. A composition for combatting fungi, comprising an inert carrier material and as an active ingredient an effective antifungal amount of a compound according to claim 21.

25. A chemical compound according to claim 21 selected from the group consisting of a 1H-1,2,4-triazole derivative having the formula:

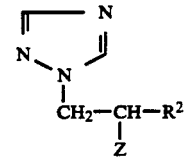

and the physiologically acceptable acid addition salts thereof, wherein:
Z is selected from the group consisting of mono- and di-halophenyl; and $R^2$ is selected from the group consisting of alkyl having from 1 to 10 carbon atoms, cycloalkyl, lower alkenyl and aralkyl, wherein the alkyl portion of said aralkyl group is $C_1$–$C_4$ alkyl and the aryl portion of said aralkyl group is phenyl and may be optionally substituted with up to three substituents selected from the group consisting of halo, methyl, methoxy, nitro and cyano.

26. A method of combatting fungal growth on plants which comprises treating said plants with an effective fungal combatting amount of a chemical compound according to claim 21.

27. A method of combatting fungal growth on plants according to claim 26 which comprises treating said plants with an effective fungal combatting amount of a chemical compound selected from the group consisting of 1-[2-(2,4-dibromophenyl)-hexyl]-1H-1,2,4-triazole and the physiologically acceptable acid addition salts thereof.

28. A method of combatting fungal growth on plants according to claim 26 which comprises treating said plants with an effective fungal combatting amount of a chemical compound selected from the group consisting of a 1H-1,2,4-triazole derivative having the formula:

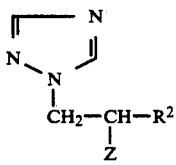

and the physiologically acceptable acid addition salts thereof, wherein:

Z' is selected from the group consisting of dichlorophenyl and dibromophenyl; and $R^2$ is selected from the group consisting of alkyl having from 1 to 8 carbon atoms, cycloalkyl and -($C_2$ to $C_4$)alkenyl-.

29. A method of combating fungal growth on plants according to claim 26 which comprises treating said plants with an effective fungal combatting amount of a chemical compound selected from the group consisting of 1H-1,2,4-triazole derivative having the formula:

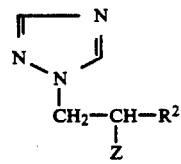

and the physiologically acceptable acid addition salts thereof, wherein:

Ar' is selected from the group consisting of mono- and di-halophenyl; and

R' is selected from the group consisting of alkyl having from 1 to 10 carbon atoms, cycloalkyl, lower alkenyl and aralkyl, wherein the alkyl portion of said aralkyl group is $C_1$–$C_4$ alkyl and the aryl portion of said aralkyl group is phenyl and may be optionally substituted with up to three substituents selected from the group consisting of halo, methyl, methoxy, nitro and cyano.

* * * * *